US00PP35417P2

(12) United States Plant Patent
Jan Kraan

(10) Patent No.: US PP35,417 P2
(45) Date of Patent: Oct. 10, 2023

(54) ***HYDRANGEA* PLANT NAMED 'BOKODAPI'**

(50) Latin Name: *Hydrangea arborescens*
Varietal Denomination: Bokodapi

(71) Applicant: Kees Jan Kraan, Alphen aan den Rijn (NL)

(72) Inventor: Kees Jan Kraan, Alphen aan den Rijn (NL)

(73) Assignees: BOOT & CO BOOMKWEKERIJEN BV, Boskoop (NL), part interest; KOLSTER HOLDING BV, Boskoop (NL), part interest ( * ) Notice: Subject to any disclaimer, the term of this patent is extended or adjusted under 35 U.S.C. 154(b) by 0 days.

(21) Appl. No.: 18/098,747

(22) Filed: Jan. 19, 2023

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — Penny J. Aguirre

(57) ABSTRACT

A new cultivar of *Hydrangea arborescens* plant named 'Bokodapi' that is characterized by its healthy and moderately vigorous growing habit, its leaves that are gray-white in color on the lower surface, its sterile flower buds that are dark pink in color, its sterile flower sepals that are grey-pink in color on the upper surface, and its sterile flower sepals that are light rose-purple in color on the lower surface.

2 Drawing Sheets

Botanical classification: *Hydrangea arborescens*.
Varietal denomination: 'Bokodapi'.

CROSS REFERENCE TO A RELATED APPLICATION

This application is related to a European plant breeders' rights application filed on Jul. 27, 2021, application No. 2021/1957. The Information for the plant breeder's Rights application was received directly from the Inventor.

BACKGROUND OF THE INVENTION

The present invention relates to a new and distinct cultivar of *Hydrangea arborescens* and will be referred to hereafter by its cultivar name, 'Bokodapi'. 'Bokodapi' represents a new smooth *Hydrangea*, a perennial shrub grown for landscape use.

'Bokodapi' was derived from an ongoing controlled breeding program directed by the Inventor in Boskoop, the Netherlands. The goal of the breeding program was to develop new cultivars of *Hydrangea arborescens* with unique characteristics. 'Bokodapi' arose in July of 2010 from open pollination of an unpatented and unnamed proprietary plant of *Hydrangea arborescens* from the Inventor's breeding program as the female parent. The male parent is unknown. 'Bokodapi' was selected as a single unique plant from amongst the resulting seedlings in July of 2020.

Asexual propagation of the new cultivar was first accomplished by softwood stem cuttings by one of the Inventors in July of 2016 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bokodapi' as a unique cultivar of *Hydrangea arborescens*.

1. 'Bokodapi' exhibits a healthy and moderately vigorous growing habit.
2. 'Bokodapi' exhibits leaves that are gray-white in color on the lower surface.
3. 'Bokodapi' exhibits sterile flower buds that are dark pink in color.
4. 'Bokodapi' exhibits sterile flower sepals that are grey-pink in color on the upper surface.
5. 'Bokodapi' exhibits sterile flower sepals that are light rose-purple in color on the lower surface.

The female parent plant of 'Bokodapi' differs from 'Bokodapi' in having inflorescences that are spherical in shape, weaker stems, and sterile flower sepals that are pale lilac-purple in color. 'Bokodapi' can be most closely compared to *Hydrangea arborescens* cultivars 'NCHA2' (U.S. Plant Pat. No. 28,316) and 'NCHA3' (U.S. Plant Pat. No. 28,317). 'NCHA2' and 'NCHA3' are both similar to 'Bokodapi' in plant habit and inflorescence shape and color. 'NCHA2' differs from 'Bokodapi' in having leaves that are light green in color on the lower surface, sterile flower sepals that are slightly larger in size and more purple rose in color, sterile flower buds that are darker pink in color, and sterile flower sepals that are dark rose red in color on the lower surface. 'NCHA3' differs from 'Bokodapi' in having leaves that are light green in color on the lower surface and sterile flower buds that are darker pink in color.

BRIEF DESCRIPTION OF THE DRAWINGS

The accompanying color photographs illustrate the overall appearance and distinct characteristics of the new *Hydrangea*. The photographs were taken of a plant 4 years in age as field grown outdoors in a trial plot in Boskoop, The Netherlands.

The photograph in FIG. 1 provides a view of the plant habit of 'Bokodapi' in bloom.

Figure 1:
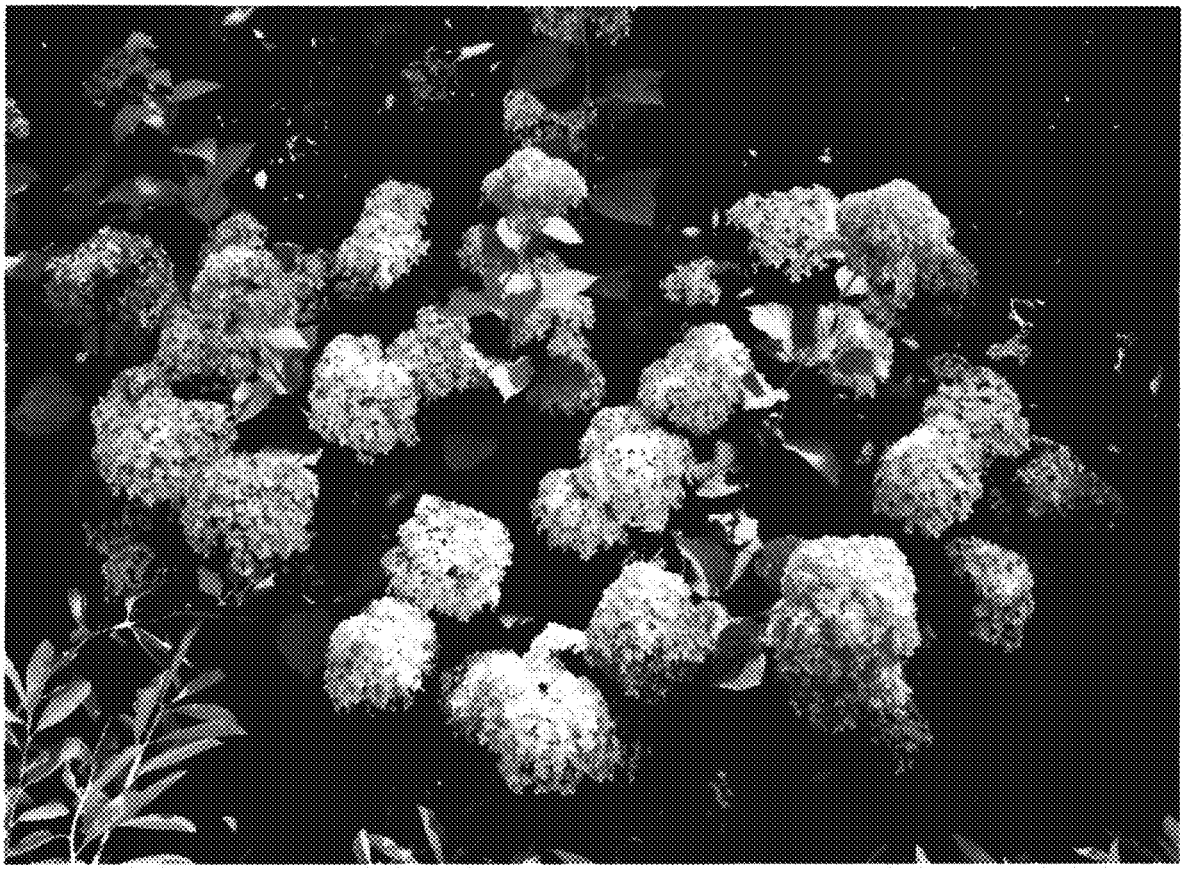
Figure 2:
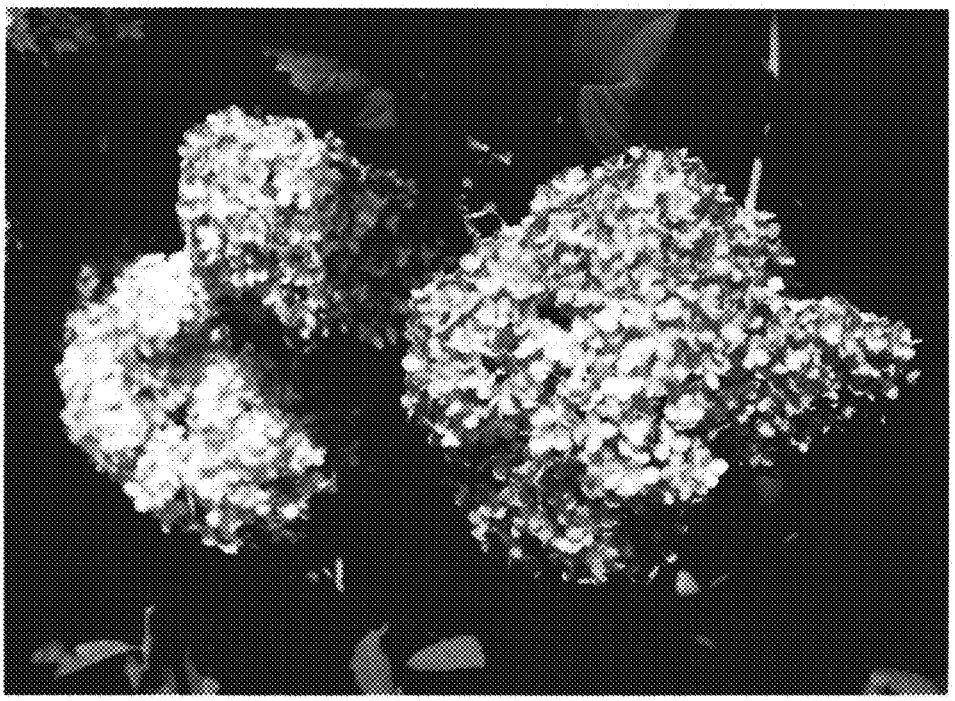

The photograph in FIG. 2 provides a close-up view of the inflorescences of 'Bokodapi'.

Figure 3:
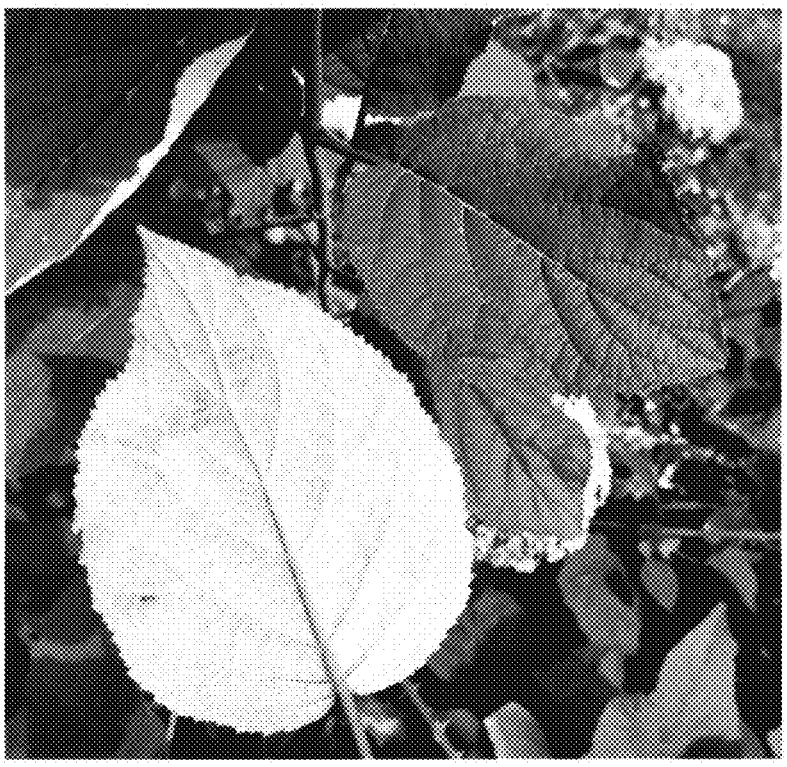

The photograph in FIG. 3 provides a close-up view of the upper and lower surface of the leaves of 'Bokodapi'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants 4 years in age as field grown outdoors in in a trial plot in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—6 weeks from mid-July into late summer in The Netherlands.

*Plant type.*—Perennial shrub with mophead-like flowerheads.

*Plant habit.*—Upright, compact, broadly spreading, and globular.

*Height and spread.*—Average of 92 cm in height, 1.25 m in width.

*Hardiness.*—U.S.D.A. Zones 5 to 9.

*Diseases and pests.*—No susceptibility and resistance to diseases or pests has been observed.

*Root description.*—Fibrous.

*Time required for root development.*—About 12 months to produce a small finished plant from a cutting.

*Growth rate.*—Moderate.

Stem description:

*Stem shape.*—Rounded.

*Stem strength.*—Strong.

*Stem aspect.*—Upright to spreading, an average angle of 55° to horizontal.

*Stem color.*—Young; 146B, mature; a blend of 194B to 194C, and 195B to 195C, occasionally tinged 186C, older bark; N199C.

*Stem size.*—An average of 66.9 cm (excluding the inflorescence) in length and 7 mm in diameter.

*Stem surface.*—Glabrous.

*Branching.*—Freely branched; an average of 25 lateral branches per plant.

*Internode length.*—An average of 6.6 cm.

Foliage description:

*Leaf shape.*—Broadly ovate, flattened to very slightly carinate.

*Leaf arrangement.*—Opposite, occasionally in whorls of 3.

*Leaf division.*—Simple.

*Leaf number.*—An average of 10 per lateral branch.

*Leaf base.*—Truncate to shallow cordate.

*Leaf apex.*—Apiculate.

*Leaf margins.*—Dentate to serrate.

*Leaf venation.*—Pinnate, upper surface color 197B, lower surface color a blend of 152B and 199B.

*Leaf size.*—An average of 14.4 cm in length, 10.1 cm in width.

*Leaf attachment.*—Petiolate.

*Leaf surface.*—Upper surface; smooth and glabrous, main vein moderately pubescent with very short adpressed hairs, 0.3 mm in length, 156A in color, lower surface; densely covered with woolly pubescent hairs 0.3 mm in length and 191C to 191D in color.

*Leaf color.*—Young upper surface; 137B and 146A, young lower surface; 191C, mature upper surface; 146A, mature lower surface; 191B.

*Petioles.*—An average of 5 cm in length and 3 mm in diameter, color; upper surface 166A and 183A, margins 187A, lower surface 152A, tinged 183C, surfaces; upper and lower slightly glossy and moderately covered with short hairs, 0.3 mm in length, and 156A in color.

Inflorescence description:

*Inflorescence type.*—Round, slightly flattened, mophead, compound corymb of rotate-shaped sterile flowers.

*Lastingness of inflorescence.*—Sterile and fertile flowers; an average of 6 weeks, sterile flowers persistent, fertile flowers; an average of 5 days, self-cleaning.

*Inflorescence number.*—One per lateral stem.

*Inflorescence size.*—An average of 14.5 cm in height and 20.7 cm in diameter.

*Flower number.*—An average of 2,750 sterile flowers and 850 fertile flowers per inflorescence.

*Flower fragrance.*—Faint, sweet and pleasant.

*Flower aspect.*—Sterile flowers; upright, outwards and drooping, fertile flowers; upright.

*Flower size.*—Sterile flowers; an average of 1.4 cm in diameter and 4.5 mm in depth, fertile flowers; 4 mm in diameter and depth.

*Flower shape.*—Sterile flowers; rotate, fertile flowers; rotate, petals drop when mature.

*Flower buds.*—Sterile flowers; 9 mm in length, 3 mm in diameter, cup-shaped, color; 185C and 185D, fertile flowers; 2 mm in diameter, 1.5 mm in depth, broadly obovate in shape, color; 186B with calyx 150B.

*Peduncles.*—An average of 10.5 cm in length and 3 mm in diameter, color is 197B, slightly tinged with 180B, moderately strong, main peduncle held in a vertical angle, lateral peduncles held in an average angle of 70° to main peduncle, surface is moderately pubescent with very short hairs an average of 0.3 mm in length, 156C in color.

*Pedicels.*—Sterile flowers; An average of 1 cm in length and 0.75 mm in diameter, held in an average angle of 30° to main peduncle, moderately strong, color; N155B and 157D, surface is dull and moderately covered with short, thin, adpressed hairs 0.4 mm in length and too small to measure color, fertile flowers; an average of 4 mm in length and 0.75 mm in diameter, held in an average angle of 5° to main peduncle, moderately strong, color; a blend of N155B and 157D, dull surface.

*Petals.*—Sterile flowers; 4, rotate, ovate to strongly concave, acute apex, cuneate base, entire margins, 1.25 mm in length, 0.75 mm in width, both surfaces are smooth, glabrous, slightly glossy, color: when opening upper surface; N155B, top 186D, when opening lower surface; 186A, base 186D, when fully open upper and lower surface; petals dropped at maturity, fertile flowers; 5, rotate, ovate to strongly concave, acute apex, cuneate base, entire margins, 1.25 mm in length, 0.75 mm in width, both surfaces are smooth, glabrous, slightly glossy, color: when opening upper surface; N155B, top 186D, when opening lower surface; 186A, base 186D, when fully open upper and lower surface; petals dropped at maturity.

*Sepals*.—Sterile flowers; 4, occasionally 3, rotate, obovate to elliptic in shape, apex is obtuse to broadly bluntly acute, cuneate base, entire margins, 8.5 mm in length, 6.5 mm in width, both surfaces glabrous and matte, color: when opening upper surface; 185C, center 186D, when opening lower surface; 186B, occasionally tinged 54A, when fully open upper surface; N155C, margins 185C, fading to 158B to 158C, slightly tinged 186D, when fully open lower surface; 186B, fading to 186D, fertile flowers; 5, rotate, deltoid in shape, apex is broadly acuminate, broadly cuneate base, entire margins, 0.6 mm in length, 0.5 mm in width, both surfaces glabrous and matte, color: when opening and fully open upper surface; 150C, when opening and fully open lower surface; 185C, tinged 150C.

Reproductive organs:

*Gynoecium*.—Sterile flowers; none observed, fertile flowers; pistils; 2, 1.25 mm in length, stigma; club-shaped, 155D in color, style; 0.5 mm in length, 155C to 155D in color, ovary; 150D in color.

*Androecium*.—Sterile flowers; stamens; 8, filaments; 1 mm in length, NN155B in color, anthers; oblong in shape, 0.5 mm in length, 155A in color, pollen; low, 155D in color, fertile flowers; stamens; 10, filaments; 3 mm in length, NN155B in color, anthers; oblong in shape, 0.5 mm in length, 155A in color, pollen; low, 155D in color.

*Fruit and seed*.—No seeds or fruit observed to date.

It is claimed:

1. A new and distinct cultivar of *Hydrangea* plant named 'Bokodapi' substantially as herein illustrated and described.

* * * * *